United States Patent
Suzuki et al.

(10) Patent No.: US 7,947,159 B2
(45) Date of Patent: May 24, 2011

(54) NOX-DECOMPOSING ELECTRODE AND METHOD FOR PRODUCING NOX SENSOR

(75) Inventors: Yoshio Suzuki, Nagoya (JP); Hideyuki Suzuki, Kasugai (JP); Kunihiko Nakagaki, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 624 days.

(21) Appl. No.: 11/964,314

(22) Filed: Dec. 26, 2007

(65) Prior Publication Data

US 2008/0156644 A1 Jul. 3, 2008

(30) Foreign Application Priority Data

Dec. 28, 2006 (JP) ................................. 2006-353873

(51) Int. Cl.
*G01N 27/333* (2006.01)

(52) U.S. Cl. .......................... 204/416; 204/419; 502/101

(58) Field of Classification Search .................. 204/426, 204/427, 429, 416, 291, 419; 29/890; 502/101
See application file for complete search history.

(56) References Cited

U.S. PATENT DOCUMENTS

| | | | |
|---|---|---|---|
| 4,283,441 A | 8/1981 | Wolf-Dieter et al. | |
| 5,419,827 A | 5/1995 | Nanataki et al. | |
| 6,419,818 B2 | 7/2002 | Kato et al. | |
| 6,607,643 B2 | 8/2003 | Takahashi et al. | |
| 7,153,402 B2 * | 12/2006 | Nakagaki et al. | 204/425 |
| 7,156,966 B2 | 1/2007 | Nakagaki et al. | |
| 2004/0069629 A1 | 4/2004 | Tanaka et al. | |

FOREIGN PATENT DOCUMENTS

| | | |
|---|---|---|
| DE | 36 35 157 A1 | 4/1988 |
| EP | 0 853 239 | 7/1998 |
| JP | 04-357165 | 12/1992 |
| JP | 11-166913 | 6/1999 |
| JP | 11-183434 | 7/1999 |
| JP | 2000-180411 | 6/2000 |
| JP | 2001-318075 | 11/2001 |
| JP | 2003-322634 | 11/2003 |
| JP | 2003-322636 | 11/2003 |
| JP | 2004-151018 | 5/2004 |
| JP | 2006-284223 | 10/2006 |

OTHER PUBLICATIONS

Hideo Inuzuka, "*Observation of Clay Minerals Using the Electron Microscope*," American Mineralogist, vol. 26, No. 7, Jul. 31, 1941, pp. 448-449 (p. 449 is not available) (XP-002475752).
KCM Corporation, "*Kibushi Clay*," Jan. 1, 1970 (XP-002475753).

* cited by examiner

*Primary Examiner* — Bruce F Bell
(74) *Attorney, Agent, or Firm* — Burr & Brown

(57) ABSTRACT

A NOx-decomposing electrode is provided having a certain or a high NOx-decomposing/reducing ability, which is formed on a third solid electrolyte layer for decomposing a NOx to produce oxygen. The detecting electrode contains a noble metal Pt, a material $ZrO_2$ of the third solid electrolyte layer, and a mixture containing silica ($SiO_2$) and alumina ($Al_2O_3$). Specifically, the detecting electrode contains 80% to 90% by weight of the Pt, 9.5% to 19.8% by weight of the $ZrO_2$, and 0.2% to 0.5% by weight of the mixture containing silica and alumina.

8 Claims, 4 Drawing Sheets

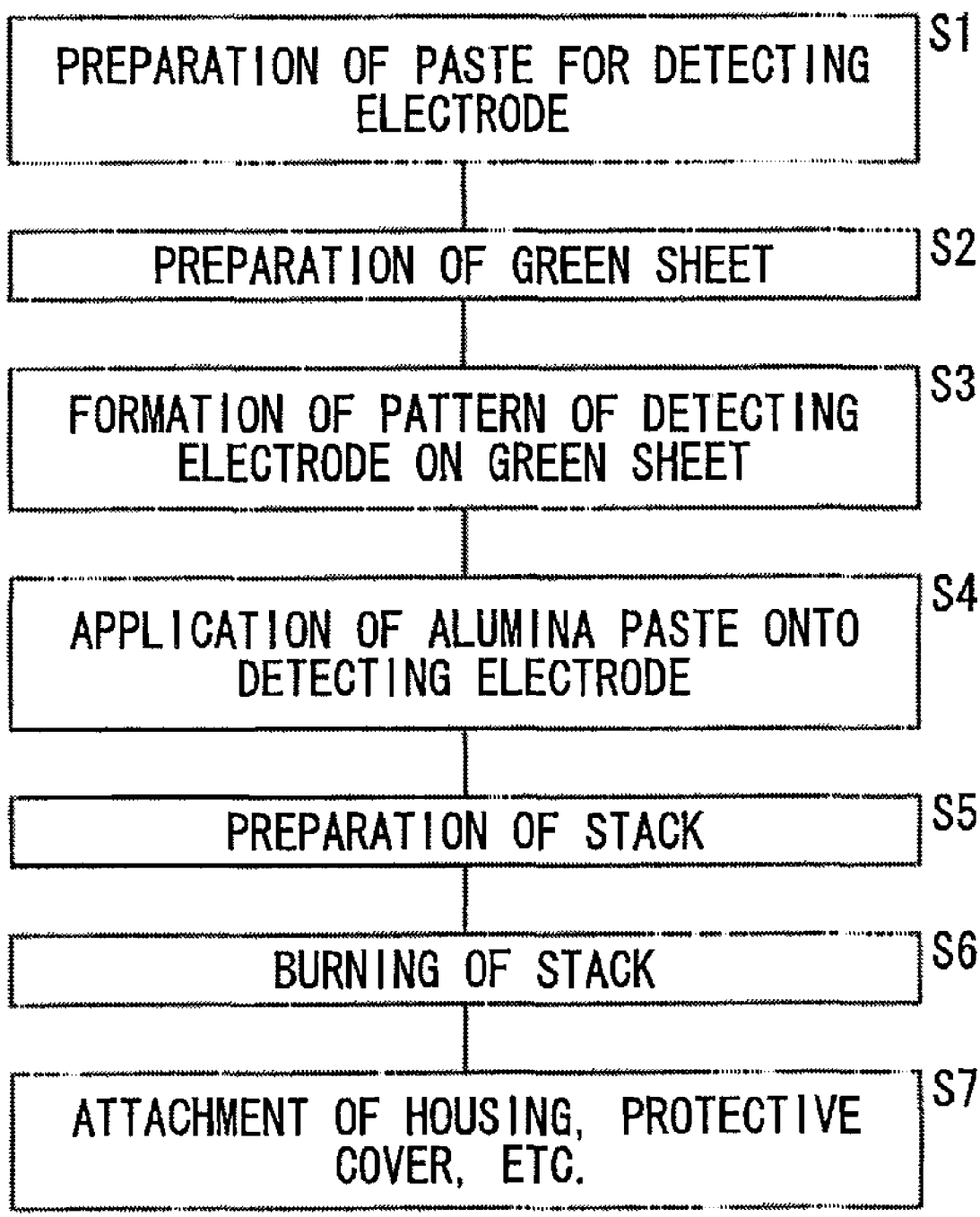

FIG. 3

| | NOBLE METAL | | SUBSTRATE MATERIAL | MIXTURE CONTAINING SILICA AND ALUMINA (IN 0.3% BY WEIGHT) | | | | | | | | |
|---|---|---|---|---|---|---|---|---|---|---|---|---|
| | Pt (% BY WEIGHT) | Rh (% BY WEIGHT) | ZrO$_2$ (% BY WEIGHT) | SiO$_2$ (%) | Al$_2$O$_3$ (%) | Fe$_2$O$_3$ (%) | TiO$_2$ (%) | CaO (%) | MgO (%) | K$_2$O (%) | IGNITION LOSS (%) |
| EXAMPLE 1 | 85 | — | 14.7 | 53 | 30.5 | — | — | — | — | — | — |
| EXAMPLE 2 | 85 | — | 14.7 | 56 | 30.5 | — | — | — | — | — | — |
| EXAMPLE 3 | 85 | — | 14.7 | 57 | 30.5 | — | — | — | — | — | — |
| EXAMPLE 4 | 85 | — | 14.7 | 53 | 26.5 | — | — | — | — | — | — |
| EXAMPLE 5 | 85 | — | 14.7 | 53 | 27.5 | — | — | — | — | — | — |
| EXAMPLE 6 | 85 | — | 14.7 | 53 | 33.5 | — | — | — | — | — | — |
| EXAMPLE 7 | 85 | — | 14.7 | 53 | 34.5 | — | — | — | — | — | — |
| EXAMPLE 8 | 85 | — | 14.7 | 53 | 30.5 | 1.8 | 1.0 | 0.32 | 0.5 | 0.87 | 11.72 |
| EXAMPLE 9 | 85 | — | 14.7 | 53 | 30.5 | 2.0 | 1.0 | 0.3 | 0.47 | 0.86 | 12.04 |
| EXAMPLE 10 | 85 | — | 14.7 | 51.7 | 31.1 | 1.86 | 1.02 | 0.3 | 0.47 | 0.86 | 12.04 |
| EXAMPLE 11 | 85 | — | 14.7 | 52.6 | 29.8 | 1.84 | 1.04 | 0.3 | 0.47 | 0.86 | 12.04 |
| EXAMPLE 12 | 85 | — | 14.7 | 53.1 | 29.9 | 1.94 | 1.02 | 0.24 | 0.58 | 1.14 | 11.44 |
| EXAMPLE 13 | 42.5 | 42.5 | 14.7 | 52.6 | 29.8 | 1.84 | 1.04 | 0.3 | 0.47 | 0.86 | 12.04 |
| COMPARATIVE EXAMPLE 1 | 85 | 25 | — | — | — | — | — | — | — | — | — |
| COMPARATIVE EXAMPLE 2 | 85 | — | 14.7 | 49 | 30.5 | — | — | — | — | — | — |
| COMPARATIVE EXAMPLE 3 | 85 | — | 14.7 | 50 | 30.5 | — | — | — | — | — | — |
| COMPARATIVE EXAMPLE 4 | 21.25 | 63.75 | 14.7 | 52.6 | 29.8 | 1.84 | 1.04 | 0.3 | 0.47 | 0.86 | 12.04 |
| COMPARATIVE EXAMPLE 5 | 63.75 | 21.25 | 14.7 | 52.6 | 29.8 | 1.84 | 1.04 | 0.3 | 0.47 | 0.86 | 12.04 |

FIG. 4

| | ADHESION STRENGTH (kg/cm) | Δ Ip2 SENSITIVITY CHANGE (%) | |
|---|---|---|---|
| | | INITIAL | 10000 CYCLE |
| EXAMPLE 1 | 480 | 0 | 40 |
| EXAMPLE 2 | 580 | 0 | 30 |
| EXAMPLE 3 | 600 | 0 | 20 |
| EXAMPLE 4 | 520 | 0 | 30 |
| EXAMPLE 5 | 500 | 0 | 40 |
| EXAMPLE 6 | 430 | 0 | 50 |
| EXAMPLE 7 | 250 | 0 | 60 |
| EXAMPLE 8 | 500 | 0 | 4.5 |
| EXAMPLE 9 | 500 | 0 | 5 |
| EXAMPLE 10 | 500 | 0 | 3 |
| EXAMPLE 11 | 500 | 0 | 1.5 |
| EXAMPLE 12 | 500 | 0 | 2.5 |
| EXAMPLE 13 | 500 | 0 | 1.5 |
| COMPARATIVE EXAMPLE 1 | 150 | 0 | -100 |
| COMPARATIVE EXAMPLE 2 | 300 | 0 | -100 |
| COMPARATIVE EXAMPLE 3 | 450 | 0 | -100 |
| COMPARATIVE EXAMPLE 4 | 500 | 0 | -100 |
| COMPARATIVE EXAMPLE 5 | 500 | 0 | -100 |

※ "-100" MEANS THAT ELECTRODE WAS BROKEN.

NOX-DECOMPOSING ELECTRODE AND METHOD FOR PRODUCING NOX SENSOR

CROSS-REFERENCE TO RELATED APPLICATIONS

This application is based upon and claims the benefit of priority from Patent Application No. 2006-353873 filed on Dec. 28, 2006 in the Japanese Patent Office, of which the contents are incorporated herein by reference.

BACKGROUND OF THE INVENTION

1. Field of the Invention

The present invention relates to a NOx-decomposing electrode having a certain or high NOx-decomposing/reducing ability for decomposing a NOx to produce oxygen, and a NOx sensor for measuring a NOx in exhaust gas from vehicles, atmospheric air, etc.

2. Description of the Related Art

A method for measuring a NOx in a gas to be measured such as a combustion gas, which comprises using a sensor obtained by forming a NOx-decomposing electrode on an oxygen ion-conductive solid electrolyte such as zirconia, thereby measuring an electromotive force generated on the NOx-decomposing electrode, has been known (see Japanese Laid-Open Patent Publication No. 11-183434, etc.) The NOx-decomposing electrode is a cermet electrode composed of a Pt—Rh alloy and a ceramic component.

A NOx-decomposing electrode, which has a multilayer structure of a plurality of cermet electrode layers containing a Pt—Rh alloy and a ceramic component, the cermet electrode layers being different in the ratio between the Pt—Rh alloy and the ceramic component, has been disclosed (see Japanese Laid-Open Patent Publication Nos. 2003-322634 and 2003-322636, etc.) In this NOx-decomposing electrode, the ceramic component is preferably a partially or fully stabilized $ZrO_2$, and the stabilizer may be $Y_2O_3$, MgO, CaO, $CeO_2$, etc. It is preferable to use $Y_2O_3$ as the stabilizer in view of burning at a low temperature.

Further, an electrode-protecting layer formed by screen printing for covering a NOx-decomposing electrode, which is a porous ceramic layer having a substantially trapezoidal cross section, has been disclosed (see Japanese Laid-Open Patent Publication No. 2006-284223, etc.) The electrode-protecting layer has a flat upper base portion extending in the horizontal direction and has tapered portions at the both ends of the upper base portion. The height of each tapered portion decreases gradually from the upper base portion toward the end of the NOx-decomposing electrode.

NOx-decomposing electrodes are used at a high temperature of 700° C. to 800° C. to measure a NOx, and thereby are continually expanded and shrunk repeatedly. As a result of the repeated expansion and shrinkage, an electrode-protecting layer on the NOx-decomposing electrode is cracked or broken, or the NOx-decomposing electrode is peeled off from a solid electrolyte, in some cases.

In these cases, the whole or part of the NOx-decomposing electrode cannot function normally, thereby the impedance of a pumping cell in a NOx sensor is increased.

SUMMARY OF THE INVENTION

In view of the above problem, an object of the present invention is to provide a NOx-decomposing electrode capable of improving the impedance stability of a pumping cell and the measurement sensitivity stability of a NOx sensor during the use of the NOx sensor, and a method for producing a NOx sensor.

A NOx-decomposing electrode according to a first aspect of the present invention has a certain or high NOx-decomposing/reducing ability, is formed on a substrate for decomposing a NOx to produce oxygen, and comprises a noble metal, a material used in the substrate, and a mixture containing silica and alumina.

Thus, the impedance of a pumping cell and the measurement sensitivity of a NOx sensor can be stabilized during the use of the NOx sensor.

In the first aspect of the present invention, the NOx-decomposing electrode may be produced by applying a paste containing the noble metal, the material used in the substrate, and the mixture containing silica and alumina to the substrate, and by burning the applied paste.

In the first aspect of the present invention, the NOx-decomposing electrode preferably comprises 80% to 90% by weight of the noble metal, 9.5% to 19.8% by weight of the material used in the substrate, and 0.2% to 0.5% by weight of the mixture.

In the NOx-decomposing electrode, the mixture preferably contains, in addition to the silica and alumina, at least one material selected from the group consisting of $Fe_2O_3$, $TiO_2$, CaO, MgO, and $K_2O$. Specifically, it is preferred that the NOx-decomposing electrode comprises 0.2% to 0.5% by weight of the mixture containing silica and alumina, and the mixture contains 50% to 56% by weight of the silica and 27.5% to 33.5% by weight of the alumina. Further, it is preferred that the mixture contains 2.5% by weight or less of the $Fe_2O_3$, 1.3% by weight or less of the $TiO_2$, 0.8% by weight or less of the CaO, 0.8% by weight or less of the MgO, and 1.5% by weight or less of the $K_2O$.

In the first aspect of the present invention, the NOx-decomposing electrode is formed on the substrate and may be covered with an electrode-protecting layer containing alumina.

A method according to a second aspect of the present invention is for producing a NOx sensor comprising a NOx-decomposing electrode having a certain or high NOx-decomposing/reducing ability, formed on a substrate for decomposing a NOx to produce oxygen, and comprises the steps of: preparing a paste containing a noble metal, a material used in the substrate, and kibushi clay; applying the paste to the substrate; and burning the substrate and the applied paste to form the NOx-decomposing electrode.

Thus, a NOx sensor excellent in the impedance stability of a pumping cell and the measurement sensitivity stability of the NOx sensor in use can be easily produced.

In the second aspect of the present invention, the paste preferably contains 80% to 90% by weight of the noble metal, 9.5% to 19.8% by weight of the material used in the substrate, and 0.2% to 0.5% by weight of the kibushi clay.

In this case, the kibushi clay to be added to the paste preferably contains 10% to 14% by weight of ignition loss (Ig. loss), 50% to 56% by weight of $SiO_2$, 27.5% to 33.5% by weight of $Al_2O_3$, 2.5% by weight or less of $Fe_2O_3$, 1.3% by weight or less of $TiO_2$, 0.8% by weight or less of CaO, 0.8% by weight or less of MgO, and 1.5% by weight or less of $K_2O$.

In the second aspect of the present invention, the method preferably further comprises the step of forming an electrode-protecting layer containing alumina such that the NOx-decomposing electrode is covered therewith.

As described above, by using the NOx-decomposing electrode of the present invention, the impedance of a pumping cell and the measurement sensitivity of a NOx sensor can be stabilized during the use of the sensor.

Further, by the method of the present invention for producing a NOx sensor, a NOx sensor excellent in the impedance stability of a pumping cell and the measurement sensitivity stability of the NOx sensor in use can be easily produced.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 2 is a process chart of production of the NOx sensor according to the embodiment, particularly a portion around a detecting electrode.

FIG. 3 is a table showing the compositions of detecting electrodes of Examples 1 to 13 and Comparative Examples 1 to 5.

FIG. 4 is a table showing the results of an adhesion strength test and a sensitivity test using the detecting electrodes of Examples 1 to 13 and Comparative Examples 1 to 5.

DETAILED DESCRIPTION OF THE INVENTION

Figure 1:
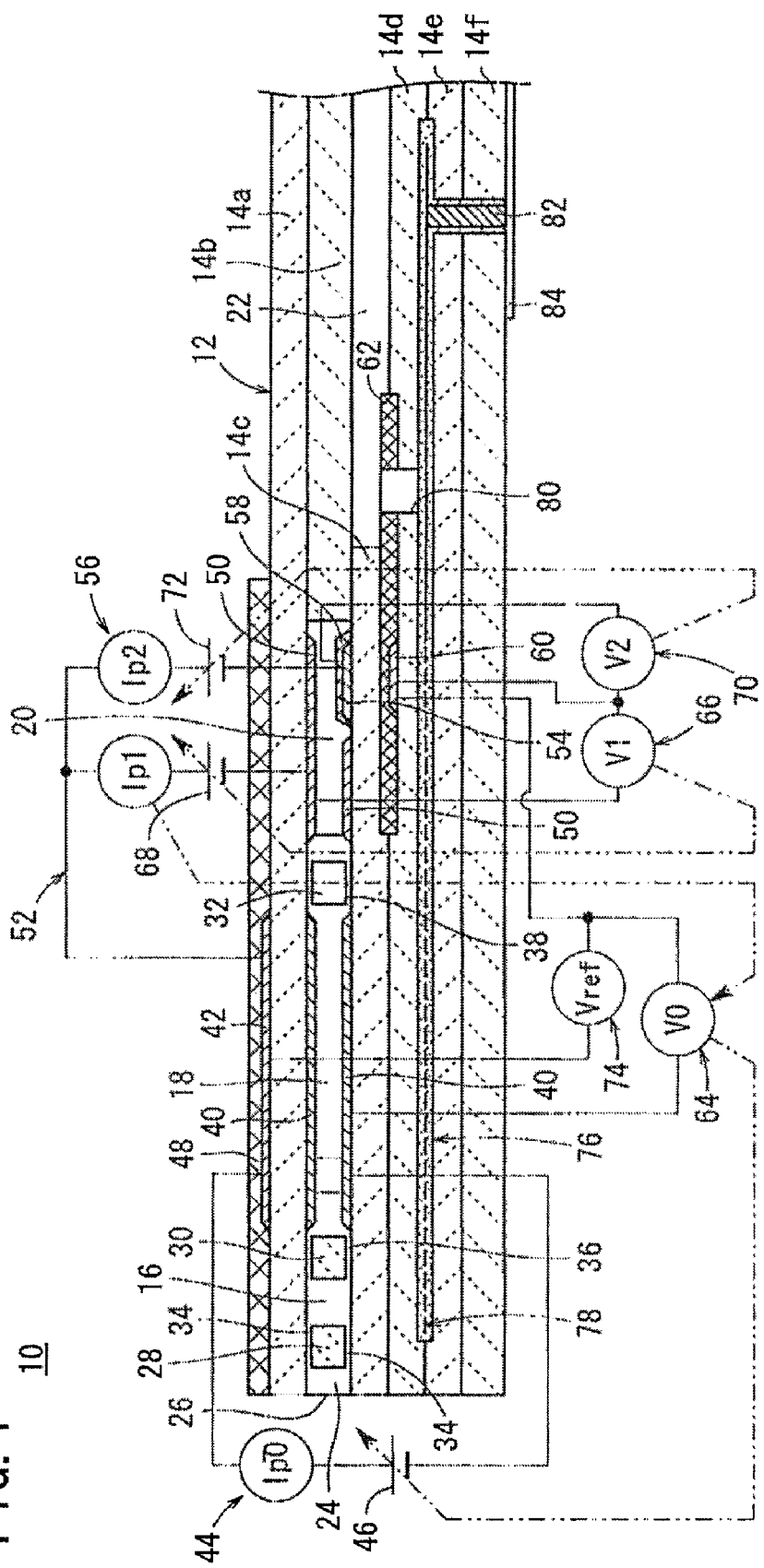
FIG. 1 is a structural view showing a NOx sensor according to an embodiment of the present invention.

An illustrative embodiment of the NOx-decomposing electrode and the NOx sensor producing method of the present invention will be described below with reference to FIGS. 1 to 4.

As shown in FIG. 1, a NOx sensor 10 according to this embodiment contains a thin and long plate-shaped sensor element 12.

The sensor element 12 has an integral plate-shaped structure containing a stack of a plurality of dense, airtight, oxygen ion-conductive, solid electrolyte layers (e.g., first to sixth solid electrolyte layers 14a to 14f). Each of the first to sixth solid electrolyte layers 14a to 14f contains a known oxygen ion-conductive solid electrolyte material such as porcelain zirconia ($ZrO_2$). The integral sensor element 12 can be easily formed by a known process of burning a stack of unburned solid electrolyte layers to integrate the layers.

At least four internal spaces (a first internal space 16, a second internal space 18, a third internal space 20, and a fourth internal space 22) are formed in the sensor element 12.

The first to third internal spaces 16, 18, and 20 are formed between the first solid electrolyte layer 14a positioned uppermost in FIG. 1 and the third solid electrolyte layer 14c positioned at the third from the top such that the first third solid electrolyte layer 14a and the third solid electrolyte layer 14c are stacked and integrated with a spacer of the second solid electrolyte layer 14b in-between.

The first to third internal spaces 16, 18, and 20 have heights corresponding to the thickness of the second solid electrolyte layer 14b, and extend in the longitudinal direction of the sensor element 12 between the first solid electrolyte layer 14a and the third solid electrolyte layer 14c as spaces without the second solid electrolyte layer 14b.

Thus, the first to third internal spaces 16, 18, and 20 have rectangular shapes, are separated from each other, and extend in the longitudinal direction of the sensor element 12 into certain widths respectively.

Among the first to third internal spaces 16, 18, and 20, the first internal space 16 is closest to a gas inlet 26 to be hereinafter described, and acts as a buffer space for buffering rapid oxygen concentration change by external pulsation of an exhaust gas. The second internal space 18 acts as a control space for controlling the oxygen partial pressure of the gas to be measured, and the third internal space 20 acts as a measurement space for fine-controlling the oxygen partial pressure of the gas to be measured and measuring an oxide such as a nitrogen oxide (NOx) in the gas.

The fourth internal space 22 is separated from the first to third internal spaces 16, 18, and 20, and extends in the longitudinal direction of the sensor element 12 between the second solid electrolyte layer 14b and the fourth solid electrolyte layer 14d as a space without the third solid electrolyte layer 14c. The fourth internal space 22 acts as a reference gas inlet path for introducing a reference gas into the sensor element 12, and the path is opened at the proximal end of the sensor element 12 to atmospheric air like conventional ones.

Thus, in the following description, the first internal space 16 is referred to as the buffer space 16, the second internal space 18 is referred to as the control space 18, the third internal space 20 is referred to as the measurement space 20, and the fourth internal space 22 is referred to as the reference gas inlet path 22.

A clogging-preventive space 24 opening outward is formed between the first solid electrolyte layer 14a and the third solid electrolyte layer 14c at the outer side of the buffer space 16, i.e. the distal end side of the sensor element 12. The opening of the clogging-preventive space 24 acts as the gas inlet 26 for introducing the external gas to be measured into the sensor element 12.

The clogging-preventive space 24 is separated from the buffer space 16 by a first partition wall 28 of the second solid electrolyte layer 14b, the buffer space 16 is separated from the control space 18 by a second partition wall 30 of the second solid electrolyte layer 14b, and the control space 18 is separated from the measurement space 20 by a third partition wall 32 of the second solid electrolyte layer 14b.

First slits 34 are formed on the upper and lower surfaces of the first partition wall 28 (between the first partition wall 28 and the first solid electrolyte layer 14a, and between the first partition wall 28 and the third solid electrolyte layer 14c), respectively. The first slits 34 act as a first diffusion rate-determining means for the gas to be measured. The external gas to be measured is introduced from the gas inlet 26 through the clogging-preventive space 24 to the buffer space 16 under a predetermined diffusion resistance of the first slits 34.

Second slits 36 are formed on the upper and lower surfaces of the second partition wall 30 for separating the buffer space 16 and the control space 18 (between the second partition wall 30 and the first solid electrolyte layer 14a, and between the second partition wall 30 and the third solid electrolyte layer 14c), respectively. The second slits 36 act as a second diffusion rate-determining means for the gas to be measured. The gas to be measured in the buffer space 16 is introduced to the control space 18 under a predetermined diffusion resistance of the second slits 36.

Third slits 38 are formed on the upper and lower surfaces of the third partition wall 32 for separating the control space 18 and the measurement space 20 (between the third partition wall 32 and the first solid electrolyte layer 14a, and between the third partition wall 32 and the third solid electrolyte layer 14c), respectively. The third slits 38 act as a third diffusion rate-determining means for the gas to be measured. The gas to be measured having a controlled oxygen concentration (partial pressure) in the control space 18 is introduced to the measurement space 20 under a predetermined diffusion resistance of the third slits 38.

In the NOx sensor 10 of this embodiment, an inner pumping electrode 40 containing a porous cermet is formed on the inner wall of the control space 18, and an outer pumping electrode 42 is formed in a portion corresponding to the inner pumping electrode 40 on the upper surface of the first solid electrolyte layer 14a. The inner pumping electrode 40, the outer pumping electrode 42, and the first to third solid electrolyte layers 14a to 14c form an electrochemical pumping cell, i.e. a main pumping cell 44.

In the main pumping cell 44, a desired control voltage (pumping voltage) Vp1 is applied between the inner pumping electrode 40 and the outer pumping electrode 42 by an external first variable power source 46, so that a pumping current Ip0 flows between the electrodes 40, 42 in the positive or negative direction. Thus, oxygen in the gas in the control space 18 is pumped to the outside, or alternatively external oxygen is pumped into the control space 18, to control the oxygen concentration (partial pressure) in the control space 18.

The buffer space 16, the first partition wall 28, the second partition wall 30, the first slits 34, and the second slits 36 provide the following effect.

In general, oxygen is rapidly introduced from a gas inlet 26 into an internal space of a sensor element 12 due to pulsation of an external exhaust gas. However, in this embodiment, the external oxygen is not introduced directly into the internal space (processing space), and the oxygen is introduced through the first slits 34 into the buffer space 16 and further introduced through the second slits 36 into the control space 18. Therefore, the rapid oxygen concentration change by exhaust gas pulsation can be counteracted by the buffer space 16, the first slits 34, and the second slits 36, whereby the influence of the pulsation of exhaust gas on the control space 18 is substantially negligibly small. As a result, the correlation is improved between the oxygen pumping amount in the control space 18 of the main pumping cell 44 and the oxygen concentration in the gas to be measured, so that the measurement accuracy can be improved, and the control space 18 can be used also as a sensor for detecting air-fuel ratio, etc. To obtain the effect advantageously, each of the first slit 34 and the second slit 36 formed on the first partition wall 28 and the second partition wall 30 preferably has a width of 10 µm or less.

By forming the clogging-preventive space 24 opening outward at the distal end of the sensor element 12, the inlets of the buffer space 16 can be prevented from clogging with particles of soot, oil combustion waste, or the like in the introduced gas to be measured through the gas inlet 26. As a result, a NOx component can be measured with higher accuracy.

The inner pumping electrode 40 and the outer pumping electrode 42 in the main pumping cell 44 generally contain a porous cermet, for example, composed of a metal such as Pt and a ceramic material such as $ZrO_2$. The inner pumping electrode 40 is placed in the control space 18 and brought into contact with the gas to be measured, and thereby should be composed of a material that causes no changes of the NOx component in the gas to be measured, i.e. a material having a low or no decomposing/reducing ability for the NOx component such as NO or $NO_2$. For example, the inner pumping electrode 40 may contain a perovskite compound ($La_3CuO_4$, etc.), a cermet of a ceramic material and a metal having a low catalytic activity (Au, etc.), or a cermet of a ceramic material, a Pt group metal, and a metal having a low catalytic activity (Au, etc.) In this embodiment, the outer pumping electrode 42 is covered with a porous protecting layer 48 containing alumina, etc., whereby the outer pumping electrode 42 is protected while preventing adhesion of an oil component, etc. in the external gas to be measured.

An auxiliary pumping electrode 50 containing a porous cermet is formed on the inner wall of the measurement space 20. Thus, the auxiliary pumping electrode 50, an appropriate electrode (the outer pumping electrode 42, etc.) on the outer surface of the sensor element 12, and the first to third solid electrolyte layers 14a to 14c form an auxiliary electrochemical pumping cell, i.e. an auxiliary pumping cell 52, to control the oxygen concentration (partial pressure) in the gas in the measurement space 20.

The auxiliary pumping electrode 50 is composed of a material having a low or no decomposing/reducing ability for the NOx component in the gas to be measured, like the inner pumping electrode 40 in the main pumping cell 44. For example, the auxiliary pumping electrode 50 may contain a porous cermet composed of Pt (platinum) and $ZrO_2$ with 1% of Au (gold).

In this embodiment, a detecting electrode 54 is formed in the measurement space 20. The detecting electrode 54, the outer pumping electrode 42, the first to third solid electrolyte layers 14a to 14c form an electrochemical pumping cell, i.e. a measuring pumping cell 56, whereby oxygen generated by decomposition of nitrogen oxide (NOx) around the detecting electrode 54 is pumped out and the amount of the oxygen is detected.

As shown in FIG. 1, the detecting electrode 54 is covered with an electrode-protecting layer 58 of a porous ceramic containing alumina in the measurement space 20. Thus, the detecting electrode 54 can be protected while preventing adhesion of an inert component such as a metal, etc. emitted from the auxiliary pumping electrode 50 in the same measurement space 20, and the catalytic activity (the NOx-decomposing/reducing ability) of the detecting electrode 54 can be efficiently maintained.

In the sensor element 12, a reference electrode 60, which can be in contact with a reference gas in the reference gas inlet path 22, is formed on the side opposite to the measurement space 20 side on the third solid electrolyte layer 14c.

The reference electrode 60 is formed on a sealing layer of the fourth solid electrolyte layer 14d, and is covered with a porous alumina layer 62 for introducing air. The reference gas in the reference gas inlet path 22 is brought into contact with the reference electrode 60 through the porous alumina layer 62.

By using the reference electrode 60, the oxygen concentration (partial pressure) in the control space 18 or the measurement space 20 can be measured.

Thus, in this embodiment, the inner pumping electrode 40 in the main pumping cell 44, the reference electrode 60, and the first to fourth solid electrolyte layers 14a to 14d form a first oxygen partial pressure-detecting cell 64 for controlling the main pumping cell 44, to detect the oxygen concentration (partial pressure) in the control space 18.

Further, the auxiliary pumping electrode 50 in the auxiliary pumping cell 52, the reference electrode 60, and the first to fourth solid electrolyte layers 14a to 14d form a second oxygen partial pressure-detecting cell 66 for controlling the auxiliary pumping cell 52, to detect the oxygen partial pressure in the measurement space 20. The voltage of a second variable power source 68 is controlled by the second oxygen partial pressure-detecting cell 66. The second variable power source 68 is used for operating the auxiliary pumping cell 52, and its pumping current Ip1 is used for controlling an electromotive force V0 in the first oxygen partial pressure-detecting cell 64.

Further, the detecting electrode 54, the reference electrode 60, and the first to fourth solid electrolyte layers 14a to 14d form a third oxygen partial pressure-detecting cell 70, to detect the oxygen partial pressure around the detecting electrode 54.

A third variable power source 72 is controlled based on an electromotive force V2 detected in the third oxygen partial pressure-detecting cell 70. The third variable power source 72 is used for operating the measuring pumping cell 56, to obtain a pumping current Ip2 corresponding to the nitrogen oxide concentration of the gas to be measured.

The outer pumping electrode 42, the reference electrode 60, and the first to fourth solid electrolyte layers 14a to 14d form an electrochemical sensor cell 74. The oxygen partial pressure (concentration) of the external gas to be measured can be detected based on an electromotive force Vref obtained by the sensor cell 74.

As shown in FIG. 1, in the sensor element 12, a plurality of ceramic layers, i.e. the fourth to sixth solid electrolyte layers 14d to 14f are stacked and integrated on the side of the third solid electrolyte layer 14c opposite to the side having the internal spaces (16, 18, 20). A heater layer 76, which generates heat under a power from an external source, is interposed between the upper fourth solid electrolyte layer 14d and the lower fifth solid electrolyte layer 14e adjacent to each other.

The heater layer 76 is used for heating the first to sixth solid electrolyte layers 14a to 14f in the sensor element 12 at a predetermined temperature to increase the oxygen ion conductivity thereof. A heater element 78 is interposed between upper and lower electric insulating layers composed of alumina, etc., whereby the heater element 78 is electrically insulated from the fourth solid electrolyte layer 14d and the fifth solid electrolyte layer 14e. A pressure diffusion hole 80 penetrates through the fourth solid electrolyte layer 14d in the proximal side of the sensor element 12, and the heater layer 76 is communicated by the pressure diffusion hole 80 to the reference gas inlet path 22, to relax an increased inner pressure in the heater layer 76. Further, the heater element 78 in the heater layer 76 is formed over the fifth solid electrolyte layer 14e and the sixth solid electrolyte layer 14f, exposed from an insulated through-hole 82, and connected to a connector pad 84 insulated from the sixth solid electrolyte layer 14f. The heater element 78 in the heater layer 76 has at least a function of heating the first to third solid electrolyte layers 14a to 14c separating the control space 18 and the measurement space 20 at a predetermined temperature.

The nitrogen oxide (NOx) concentration of the gas to be measured is detected by the NOx sensor 10 of this embodiment as follows. First, the external gas to be measured is introduced from the clogging-preventive space 24 at the distal end of the sensor element 12 through the first slits 34 formed on the upper and lower surfaces of the first partition wall 28 into the buffer space 16, and is further introduced through the second slits 36 formed on the upper and lower surfaces of the second partition wall 30 into the control space 18. Then, the voltage of the first variable power source 46 is controlled, whereby the pumping current Ip0 of the main pumping cell 44 is controlled, to stabilize the electromotive force V0 in the first oxygen partial pressure-detecting cell 64. In this process, the oxygen partial pressure in the control space 18 is adjusted at a predetermined value, e.g. about $10^{-7}$ atm.

The gas to be measured is introduced from the control space 18 through the third slits 38 formed on the upper and lower surfaces of the third partition wall 32 into the measurement space 20. The voltage of the second variable power source 68 is controlled based on an electromotive force V1 detected by the second oxygen partial pressure-detecting cell 66, and an oxygen pumping process is carried out by the auxiliary pumping cell 52 under a power supplied from the second variable power source 68, so that the oxygen partial pressure in the measurement space 20 is reduced to the extent that the oxygen has substantially no affect on the NOx measurement. The pumping current Ip1 of the auxiliary pumping cell 52 is input as a control signal into the first oxygen partial pressure-detecting cell 64 to control its electromotive force V0, whereby the gradient of the oxygen partial pressure is stabilized in the measurement space 20 over the third slits 38 and the auxiliary pumping electrode 50.

Further, the gas having the oxygen partial pressure controlled in the measurement space 20 is introduced through the electrode-protecting layer 58 to the detecting electrode 54 under a predetermined diffusion resistance. The NOx in the gas is reduced or decomposed around the detecting electrode 54 to produce oxygen.

Thus produced oxygen is pumped by the measuring pumping cell 56. In this step, the voltage of the third variable power source 72 is controlled to stabilize the electromotive force V2 in the third oxygen partial pressure-detecting cell 70. The amount of the oxygen produced around the detecting electrode 54 is proportional to the NOx concentration of the object gas to be measured, and thus the NOx concentration can be calculated using the pumping current Ip2 in the measuring pumping cell 56.

In the NOx sensor 10 of this embodiment, the detecting electrode 54 contains a noble metal such as Pt (platinum), a material such as $ZrO_2$, equal to a material used in the third solid electrolyte layer 14c, and a mixture containing silica ($SiO_2$) and alumina ($Al_2O_3$).

In this embodiment, the detecting electrode 54 contains 80% to 90% by weight of Pt (platinum), 9.5% to 19.8% by weight of $ZrO_2$, and 0.2% to 0.5% by weight of the mixture containing silica and alumina.

In the detecting electrode 54, the content of the noble metal is higher than the content of $ZrO_2$, which is the material used in the third solid electrolyte layer 14c, so that the adhesion between the third solid electrolyte layer 14c of $ZrO_2$ and the detecting electrode 54 is improved. Further, the detecting electrode 54 contains 0.2% to 0.5% by weight of the mixture containing silica and alumina, whereby even in the case of measuring the NOx at a high temperature of 700° C. to 800° C., the expansion and shrinkage of the detecting electrode 54 is reduced, the electrode-protecting layer 58 on the detecting electrode 54 is not cracked or broken, and the detecting electrode 54 is not peeled off from the third solid electrolyte layer 14c.

Thus, in this embodiment, the impedance of the measuring pumping cell 56 and the measurement sensitivity of the NOx sensor 10 can be stabilized during using the NOx sensor 10.

The above mixture preferably contains, in addition to the silica and alumina, at least one material selected from the group consisting of $Fe_2O_3$, $TiO_2$, CaO, MgO, and $K_2O$.

Specifically, it is preferred that the detecting electrode 54 contains 0.2% to 0.5% by weight of the mixture, and the mixture contains 50% to 56% by weight of the silica and 27.5% to 33.5% by weight of the alumina.

The mixture preferably contains, in addition to the silica and alumina, at least one material selected from the group consisting of $Fe_2O_3$, $TiO_2$, CaO, MgO, and $K_2O$. Specifically, it is preferred that the detecting electrode 54 contains 0.2% to 0.5% by weight of the mixture, and the mixture contains 2.5% by weight or less of the $Fe_2O_3$, 1.3% by weight or less of the $TiO_2$, 0.8% by weight or less of the CaO, 0.8% by weight or less of the MgO, and 1.5% by weight or less of the $K_2O$.

A method for producing the NOx sensor 10 according to the embodiment, particularly a method for forming the detecting electrode 54, will be described below with reference to FIG. 2.

First, in the step S1 of FIG. 2, a paste for the detecting electrode 54, which contains Pt, $ZrO_2$, and kibushi clay as starting materials, is prepared. In this step, 80% to 90% by weight of Pt, 9.5% to 19.8% by weight of $ZrO_2$, and 0.2% to 0.5% by weight of the kibushi clay are mixed, and an organic binder, a plasticizer, and an organic solvent are added thereto, to prepare the paste for the detecting electrode 54. The kibushi clay may be Onada 1st class soil, Nikkyo 1st class soil, Yutaka special A class soil, Yakusa A class soil, Shidare elutriation product, etc.

In the step S2 of FIG. 2, a green sheet of the third solid electrolyte layer 14c is prepared. The green sheet is obtained by mixing a powder of a partially or fully stabilized zirconia, an organic binder, a plasticizer, and an organic solvent, and by carrying out a doctor blade method, etc.

In the step S3 of FIG. 2, the paste for the detecting electrode 54 is applied to the green sheet of the third solid electrolyte layer 14c into a thickness of 10 to 25 µm by a screen printing method, to form a pattern of the detecting electrode.

In the step S4 of FIG. 2, an alumina paste is applied into a thickness of 20 to 50 µm by a screen printing method over the detecting electrode 54.

In the step S5 of FIG. 2, patterns of the inner pumping electrode 40, the outer pumping electrode 42, and the auxiliary pumping electrode 50 are formed on green sheets of the first to third solid electrolyte layers 14a to 14c, respectively. Further, the green sheets are laminated to obtain a stack.

In the step S6 of FIG. 2, the above stack is burned at a high temperature of 1,300° C. or higher, to obtain the sensor element 12. The above described electrodes including the detecting electrode 54 are formed in the sensor element 12 by the burning step.

In the step S7 of FIG. 2, though not shown, a housing, a protective cover, a connector, etc. are attached to the sensor element 12 to produce the NOx sensor 10 of this embodiment.

In this embodiment, the kibushi clay is used in the preparation of the paste for the detecting electrode 54. Therefore, the paste can be easily prepared such that the paste contains 0.2% to 0.5% by weight of the kibushi clay as the above described mixture, and the mixture contains 50% to 56% by weight of silica, 27.5% to 33.5% by weight of alumina, 2.5% by weight or less of $Fe_2O_3$, 1.3% by weight or less of $TiO_2$, 0.8% by weight or less of CaO, 0.8% by weight or less of MgO, and 1.5% by weight or less of $K_2O$.

Thus, the NOx sensor 10 excellent in the impedance stability of the measuring pumping cell 56 and the measurement sensitivity stability of the NOx sensor 10 in use can be easily produced.

Adhesion strength and sensitivity of detecting electrodes 54 of Examples 1 to 13 and Comparative Examples 1 to 5 were tested.

In the adhesion strength test, a jig was bonded to the center of the upper surface of an electrode-protecting layer 58 formed on each detecting electrode 54, and the jig was pulled upward. When the detecting electrode 54 was peeled off from a third solid electrolyte layer 14c, the pull force was measured as the adhesion strength.

In the sensitivity test, each of the detecting electrodes 54 of Examples 1 to 13 and Comparative Examples 1 to 5 was attached to an exhaust gas pipe of an experimental engine bench (3.5 L/V6 petrol engine), and was exposed to an exhaust gas having an NO concentration of 500 ppm, a lifecycle driving pattern, and a gas temperature of 400° C. to 800° C. The ΔIp2 sensitivity change was measured at the initial stage and after 10,000 cycles.

As shown in FIG. 3, in Examples 1 to 12, 85% by weight of Pt, 14.7% by weight of $ZrO_2$, and 0.3% by weight of a mixture containing silica and alumina were mixed to prepare a paste, so that the detecting electrode 54 was produced.

In Example 1, the mixture contained 53% by weight of $SiO_2$, and 30.5% by weight of $Al_2O_3$.

In Example 2, the mixture contained 56% by weight of $SiO_2$, and 30.5% by weight of $Al_2O_3$.

In Example 3, the mixture contained 57% by weight, of $SiO_2$, and 30.5% by weight of $Al_2O_3$.

In Example 4, the mixture contained 53% by weight of $SiO_2$, and 26.5% by weight of $Al_2O_3$.

In Example 5, the mixture contained 53% by weight of $SiO_2$, and 27.5% by weight of $Al_2O_3$.

In Example 6, the mixture contained 53% by weight of $SiO_2$, and 33.5% by weight of $Al_2O_3$.

In Example 7, the mixture contained 53% by weight of $SiO_2$, and 34.5% by weight of $Al_2O_3$.

In Example 8, the mixture contained 53% by weight of $SiO_2$, 30.5% by weight of $Al_2O_3$, 1.8% by weight of $Fe_2O_3$, and 1.0% by weight of $TiO_2$.

In Example 9, the mixture contained 53% by weight of $SiO_2$, 30.5% by weight of $Al_2O_3$, 2.0% by weight of $Fe_2O_3$, and 1.0% by weight of $TiO_2$.

In Example 10, the mixture contained 51.7% by weight of $SiO_2$, 31.1% by weight, of $Al_2O_3$, 1.86% by weight of $Fe_2O_3$, 1.02% by weight of $TiO_2$, 0.32% by weight of CaO, 0.5% by weight of MgO, 0.87% by weight of $K_2O$, and 11.72% by weight of ignition loss.

In Example 11, the mixture contained 52.6% by weight of $SiO_2$, 29.8% by weight of $Al_2O_3$, 1.84% by weight of $Fe_2O_3$, 1.04% by weight of $TiO_2$, 0.3% by weight of CaO, 0.47% by weight of MgO, 0.86% by weight of $K_2O$, and 12.04% by weight of ignition loss.

In Example 12, the mixture contained 53.1% by weight of $SiO_2$, 29.9% by weight of $Al_2O_3$, 1.94% by weight of $Fe_2O_3$, 1.02% by weight of $TiO_2$, 0.24% by weight of CaO, 0.58% by weight of MgO, 1.14% by weight of $K_2O$, and 11.44% by weight of ignition loss.

As shown in FIG. 3, in Example 13, 85% by weight of noble metals (42.5% by weight of Pt and 42.5% by weight of Rh, the ratio thereof 50:50), 14.7% by weight of $ZrO_2$, and 0.3% by weight of a mixture containing silica and alumina were mixed to prepare a paste, so that the detecting electrode 54 was produced.

In Example 13, the mixture contained 52.6% by weight of $SiO_2$, 29.8% by weight of $Al_2O_3$, 1.84% by weight of $Fe_2O_3$, 1.04% by weight of $TiO_2$, 0.3% by weight of CaO, 0.47% by weight of MgO, 0.86% by weight of $K_2O$, and 12.04% by weight of ignition loss.

In Comparative Example 1, 85% by weight of Pt and 25% by weight of Rh were mixed to prepare a paste, so that the detecting electrode 54 was produced. Thus, the mixture containing silica and alumina was not used in the paste.

In Comparative Examples 2 and 3, 85% by weight of Pt, 14.7% by weight of $ZrO_2$, and 0.3% by weight of a mixture containing silica and alumina were mixed to prepare a paste, so that the detecting electrode 54 was produced.

In Comparative Example 2, the mixture contained 49% by weight of $SiO_2$, and 30.5% by weight of $Al_2O_3$.

In Comparative Example 3, the mixture contained 50% by weight of $SiO_2$, and 30.5% by weight of $Al_2O_3$.

In Comparative Examples 4 and 5, noble metals Pt and Rh, 14.7% by weight of $ZrO_2$, and 0.3% by weight of a mixture containing silica and alumina were mixed to prepare a paste, so that the detecting electrode 54 was produced.

In Comparative Example 4, the paste contained 85% by weight of the noble metals (21.25% by weight of Pt and 63.75% by weight of Rh, the ratio thereof 25:75), and the mixture had a composition equal to that of Example 13.

In Comparative Example 5, the paste contained 85% by weight of the noble metals (63.75% by weight of Pt and 21.25% by weight of Rh, the ratio thereof 75:25), and the mixture had a composition equal to that of Example 13.

The results of the adhesion strength test and the sensitivity test are shown in FIG. 4. It is clear from the results shown in FIG. 4 that the detecting electrodes of Examples 1 to 13 were not peeled off even after the 10,000 cycles. Particularly, the sensitivities of the detecting electrodes of Examples 8 to 13 were changed little even after the 10,000 cycles, and thus the detecting electrodes could maintain stable measurement sensitivities for the long period.

On the other hand, the detecting electrodes of Comparative Examples 1 to 5 were peeled off at the 10,000 cycles, and were not suitable for prolonged measurements.

It is a matter of course that the NOx-decomposing electrode and the NOx sensor-producing method according to the present invention are not limited to the embodiment described above, which may be embodied in other various forms without deviating from the gist or essential characteristics of the present invention.

What is claimed is:

1. A NOx-decomposing electrode having a certain or high NOx-decomposing/reducing ability, formed on a substrate for decomposing a NOx to produce oxygen,
wherein said NOx-decomposing electrode comprises 80 to 90 wt % of a noble metal, 9.5 to 19.8 wt % of a material used in said substrate, and 0.2 to 0.5 wt % of a mixture containing alumina and at least 51.7% by weight of silica.

2. A NOx-decomposing electrode according to claim 1, wherein said mixture contains, in addition to said silica and said alumina, at least one material selected from the group consisting of $Fe_2O_3$, $TiO_2$, CaO, MgO, and $K_2O$.

3. A NOx-decomposing electrode according to claim 2, comprising 0.2% to 0.5% by weight of said mixture, wherein said mixture contains 2.5% by weight or less of said $Fe_2O_3$, 1.3% by weight or less of said $TiO_2$, 0.8% by weight or less of said CaO, 0.8% by weight or less of said MgO, and 1.5% by weight or less of said $K_2O$.

4. A NOx-decomposing electrode according to claim 1, wherein said NOx-decomposing electrode is formed on said substrate and covered with an electrode-protecting layer containing alumina.

5. A method for producing a NOx sensor comprising a NOx-decomposing electrode having a certain or a high NOx-decomposing/reducing ability, formed on a substrate for decomposing a NOx to produce oxygen, wherein said method comprises the steps of:
preparing a paste of a mixture containing a noble metal, a material used in said substrate, and kibushi clay, as a starting material;
applying said paste to said substrate; and
firing said substrate and said paste to form said NOx-decomposing electrode.

6. A method according to claim 5, wherein said paste contains 80% to 90% by weight of said noble metal, 9.5% to 19.8% by weight of said material used in said substrate, and 0.2% to 0.5% by weight of said kibushi clay.

7. A method according to claim 6, wherein said kibushi clay added to said paste contains 50% to 56% by weight of $SiO_2$, 27.5% to 33.5% by weight of $Al_2O_3$, 2.5% by weight or less of $Fe_2O_3$, 1.3% by weight or less of $TiO_2$, 0.8% by weight or less of CaO, 0.8% by weight or less of MgO, and 1.5% by weight or less of $K_2O$.

8. A method according to claim 5, further comprising the step of forming an electrode-protecting layer containing alumina such that said NOx-decomposing electrode is covered therewith.

* * * * *